United States Patent [19]

Gubelmann et al.

[11] Patent Number: 5,019,657
[45] Date of Patent: May 28, 1991

[54] PROCESS FOR THE PREPARATION OF HALOPHENOLS

[75] Inventors: Michel Gubelmann, Lyon; Philippe-jean Tirel, Oullins, both of France

[73] Assignee: Rhone-Poulenc Chimie, Courbevoie, France

[21] Appl. No.: 346,529

[22] Filed: May 2, 1989

[30] Foreign Application Priority Data

May 2, 1988 [FR] France ............................... 88 05848

[51] Int. Cl.$^5$ .............................................. C07C 39/24
[52] U.S. Cl. ................................................... 568/774
[58] Field of Search ....................................... 568/774

[56] References Cited

U.S. PATENT DOCUMENTS

| | | | |
|---|---|---|---|
| 1,547,725 | 6/1923 | Bibb | 568/774 |
| 3,702,886 | 11/1972 | Argauer et al. | 568/774 |
| 3,939,214 | 2/1976 | Rennie | 568/774 |
| 3,953,530 | 4/1976 | Dulog et al. | 568/774 |
| 4,578,521 | 3/1986 | Chang et al. | 568/774 |

FOREIGN PATENT DOCUMENTS

3430554 2/1986 Fed. Rep. of Germany .

OTHER PUBLICATIONS

Journal of the American Chemical Society, 78:6037 (1956).
Journal of the American Chemical Society, 81:94–101 (1959).
Journal of Physcial Chemistry, 87 (6): 665–667 (1983).
Chemical Abstracts, vol. 109(10):75661u Sep. (1988).
Chemistry Letters, 6:953–956 (1988).

*Primary Examiner*—Werren B. Lone
*Attorney, Agent, or Firm*—Finnegan, Henderson, Farabow, Garrett, and Dunner

[57] ABSTRACT

A process for the preparation of halophenols. A halobenzene is brought into contact with nitrous oxide on an acidified zeolite.

13 Claims, No Drawings

PROCESS FOR THE PREPARATION OF HALOPHENOLS

The present invention relates to a process for the preparation of halophenols; it relates more particularly to a process for the direct hydroxylation of halobenzenes.

Various processes for the synthesis of halophenols, and more particularly, the synthesis of fluorophenols are known.

For example, a process has been described in a German patent, DE 3,430,554, which consists in the use of bromofluorobenzene as the starting material to carry out a hydrolysis by barium hydroxide on a copper-based catalyst. The yields of this type of reaction are excellent. However, bromofluorobenzene is a costly starting material which is difficult to synthesize because its preparation requires two synthesis steps, and gives rise to corrosion of the reactors. The industry has, therefore, long been seeking a less costly, yet effective, starting material.

A process for the fluorination of hydroxyanilines by diazotization in the presence of tetrafluoroboric acid and a copper catalyst in acetone is also known, and is described in an article by BERGMANN, published in the Journal of the American Chemical Society 78, 6037 in 1956. This technique, even though it uses an inexpensive starting material, is difficult to perform as a result of the presence of tetrafluoroboric acid. In fact, the handling and the cost of tetrafluoroboric acid make this process difficult to operate in any chemical industry not experienced regarding the safety problems associated with the handling of HF-BF$_3$ mixtures.

It is also known to carry out a diazotization reaction on parafluoroaniline in sulfuric acid. This process is described in an article by FINGER G. C. et al published in the Journal of the American Chemical Society, 81, 94–7 in 1959. Parafluoroaniline, like the bromofluorobenzenes, is disfavored by the industry for use in large volume syntheses because it is not an economical starting material.

The cost of the starting materials and the difficulty in carrying out diazotization reactions under strict safety conditions are the reasons why the chemical industry is always seeking simple and economical synthesis processes to prepare halophenols.

Chemists have long been searching, unsuccessfully, to simply and economically introduce the desired hydroxyl group directly on the benzene ring of a halobenzene. The only publication describing the direct introduction of a hydroxyl group on a benzene ring is an article by IWAMOTO published in the Journal of Physical Chemistry, 87, 6, 1983.

That article describes a reaction wherein the direct hydroxylation of benzene is effected by nitrous oxide ($N_2O$) in the presence of a catalyst based on an oxide of a metal of groups V or VI of the periodic table. Vanadium oxide is the preferred oxide. It is preferable to use this oxide arranged on a support based on silica in an amount by weight of between 1 and 10% relative to the support. The support preferably consists of silica, since alumina gives rise to the formation of a mixture of carbon oxides in the majority of cases.

Although the process described by Iwamoto was successful, it is unsatisfactory because the use of these catalysts containing vanadium oxides makes the process unattractive to the industry.

The chemical industry has therefore still been seeking a satisfactory process for the direct hydroxylation of the benzene ring on a simple and readily available substrate. The present invention has enabled this objective to be achieved. The present invention is a process for the preparation of a halophenol, wherein a halobenzene and nitrous oxide are brought into contact on an acidified zeolite for a time sufficient to form the halophenol.

The zeolite is preferably selected from the commercial types, such as:

zeolite ZSM-5 from MOBIL OIL, the preparation of which is described in U.S. Pat. No. 3,702,886, the disclosure of which is incorporated by reference herein.

zeolite US-Y sold by TOYO SODA zeolite HY sold by UNION CARBIDE CHEMICALS under the reference LZY 82.

zeolite H-Mordenite sold by LA GRANDE PAROISSE.

The commercial zeolite ZSM-5 is most preferable.

The zeolite preferably has a $SiO_2/Al_2O_3$ ratio greater than 90:1 and more preferentially of from 90:1 to 500:1.

In the process of the invention, the commercial zeolite, particularly if not already in acidic form, is preferably acidified by the addition of an organic or inorganic acid. It may also be desirable to further acidify commerical acidic zeolites. The inorganic acid is preferably selected from the group consisting of hydrochloric acid, sulfuric acid, nitric acid, perchloric acid and phosphoric acid. The organic acid is preferably selected from the group consisting of halomethanesulfonic and halocarboxylic acids and, more preferably, trifluoromethanesulfonic acid.

It is preferable to use the inorganic acids since the organic acids have no advantage over the inorganic acids, and have the disadvantage of being more costly.

According to a preferred mode of operation, the zeolite is acidified by passing a volume of acid over the zeolite, preferably from 10 ml to 100 ml per gram of zeolite. It is preferred that the acid have a normality of from 0.1 N to 2 N. This passage may be effected in a single step or preferably in several successive steps.

The halobenzenes are preferably chosen from halogenated benzene derivatives, which may be substituted by an alkyl or alkoxy group containing one to two carbon atoms. Preferred halobenzenes have the formula (I)

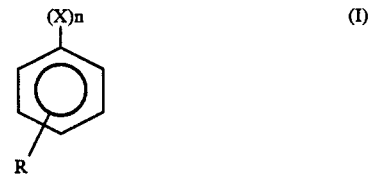

in which

R represents hydrogen or an alkyl or alkoxy group containing 1 to 2 carbon atoms;

X represents a halogen and preferably chlorine or fluorine; and n is an integer from 1 to 3.

The use of fluorobenzene is most preferred.

Nitrous oxide is used in the pure form or as a mixture with an inert gas which does not contain oxygen, such as nitrogen.

It is preferable to introduce the halobenzene as a mixture with nitrous oxide in a molar ratio of nitrous oxide to halobenzene ranging from 1:1 to 10:1.

According to one preferred operating process, the halobenzene is vaporized, mixed with the nitrous oxide in accordance with the previously-defined proportions and circulated over the zeolite. The reaction preferably takes place at a temperature ranging from 300° to 500° C.

The reaction gases containing a mixture of isomers of halophenols are condensed and separated by any technique known to those skilled in the art.

The following examples are given solely to illustrate the invention and are not to be considered as limiting the invention.

In these examples the following abbreviations are used:

$$RC = \text{rate of conversion} = \frac{\text{product converted}}{\text{product introduced}} \text{ in moles}$$

$YC$ = yield relative to product converted =

$$\frac{\text{product desired}}{\text{product converted}} \text{ in moles}$$

EXAMPLES 1 to 3

Preparation of the catalyst 10 g of commercial zeolite NaZSM-5 are poured into contact with 100 ml of a 1N HCl solution at 60° C. for 4 hours, with stirring. The mixture is allowed to cool and washed with exchange water. The solid is filtered off and dried in an oven at 100° C.

The washing described above is repeated 4 times. The dried product obtained after the 4th washing is ground.

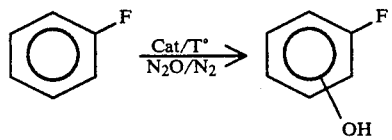

EXPERIMENTAL CONDITIONS:

| | |
|---|---|
| Vapor phase: | continuous |
| Catalyst: | HZSM-5 |
| Temperature: | pore diameter: 550 pm<br>ratio SiO$_2$/Al$_2$O$_3$ = 120<br>tests at 350° C. (Example 1);<br>400° C. (Example 2);<br>450° C. (Example 3) |
| Contact time: | 1 second |
| Molar ratios: | fluorobenzene/N$_2$/N$_2$O (2/5/8) |

1.05 g of HZSM-5 catalyst (SiO$_2$/Al$_2$O$_3$=120) in powder form, dispersed in 4 g of qranular quartz (less than 0.8 mm) are introduced into a quartz tube reactor (length = 16 cm, internal diameter = 1.8 cm).

A 10-cm bed of glass balls enabling the gas mixture to be homogenized is then added. The reactor loaded in this way is conditioned for 15 hours at 350° C. under nitrogen in a tubular furnace.

The catalyst is then treated for 30 min at the reaction temperature with 4 cc of fluorobenzene and 2.4 l/h of nitrogen.

The reaction is carried out continuously by introducing 1.5 cc/h of fluorobenzene, 1.4 l/h of nitrous oxide and 0.9 l/h of nitrogen. The molar ratio is: fluorobenzene/N$_2$/N$_2$O (2/5/8)

The results of Examples 1 to 3 are collated in Table I.

EXAMPLES 4 to 6

Under the same conditions as in Example 1, the nature of the zeolite and the acidification number are varied.

| | |
|---|---|
| Temperature | 400° C. |
| Volume ratio | fluorobenzene/nitrogen/ nitrous oxide (2/5/8) |
| Contact time | 1 second |

The results of Examples 4 to 6 are collated in Table II.

TABLE I

| | | | | | | ISOMER DISTRIBUTION | | | | |
|---|---|---|---|---|---|---|---|---|---|---|
| EX | CATALYST | rt (h) | T (°C.) | RC(φF) % | YC TOTAL (FφOH) % | ORTHO | META | PARA | YC (φOH) % | YC % TOTAL |
| 1 | ZEOLITE | 1 | 350 | 9.2 | 90.4 | 26.7 | 20.0 | 53.3 | 7.2 | 97.6 |
| 2 | SiO$_2$/AL$_2$O$_3$ = 120 | 1 | 400 | 11.0 | 90.4 | 31.1 | 22.7 | 46.2 | 4.1 | 94.5 |
| 3 | | 1 | 450 | 15.2 | 85.3 | 24.4 | 23.7 | 51.9 | 2.7 | 88.0 |
| COMP1 | SILICATE | 1 | 400 | 0 | 0 | — | — | — | — | — |
| COMP2 | none | 1 | 400 | 0 | 0 | — | — | — | — | — |

TABLE II

| | | | | | | ISOMER DISTRIBUTION | | | |
|---|---|---|---|---|---|---|---|---|---|
| EX | CATALYST | rt (h) | T (°C.) | RC(φF) % | YC TOTAL (FφOH) % | ORTHO | META | PARA | YC (φOH) % |
| 4 | SiO$_2$/AL$_2$O$_3$ = 120<br>4 Exch.H' | 1 | 400 | 11 | 90 | 31 | 23 | 46 | 4 |

TABLE II-continued

| | | | | ISOMER DISTRIBUTION | | | | | |
|---|---|---|---|---|---|---|---|---|---|
| EX | CATALYST | rt (h) | T (°C.) | RC(φF) % | YC TOTAL (FφOH) % | ORTHO | META | PARA | YC (φOH) % |
| 5 | $\frac{SiO_2}{Al_2O_3} = 120$ 8Exch.H' | 1 | 400 | 14 | 91 | 28 | 23 | 49 | 1 |
| COMP3 | $\frac{SiO_2}{Al_2O_3} = 40$ | 1 | 400 | 4 | 31 | 36 | 28 | 36 | 68 |
| 6 | HY | 1 | 400 | 1 | 50 | NOT DETERMINED | | | |

What is claimed is:

1. A process for the preparation of a halophenol, comprising the step of bringing a halobenzene and nitrous oxide into contact on an acidified zeolites having a SiO$_2$/Al$_2$O$_3$ ratio greater than 90:1 for a time sufficient to form said halophenol.

2. The process as claimed in claim 1, wherein the halobenzene has the formula (I)

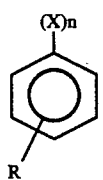

(I)

wherein
X represents a halogen;
R represents hydrogen or an alkyl or alkoxy radical containing 1 to 2 carbon atoms; and
n is an integer from 1 to 3.

3. The process as claimed in claim 2, wherein X represents chlorine or fluorine.

4. The process as claimed in claim 2, wherein the compound of formula (I) is fluorobenzene.

5. The process as claimed in claim 1, wherein the acidified zeolite is selected from the group consisting of the zeolites HZSM-5, HY and H-Mordenite.

6. The process as claimed in claim 5, wherein the acidified zeolite is HZSM-5.

7. The process as claimed in claim 1, wherein the zeolite is acidified by an organic acid.

8. The process as claimed in claim 1, wherein the zeolite is acidified by an inorganic acid.

9. The process as claimed in claim 8, wherein the inorganic acid is selected from the group consisting of hydrochloric acid, sulfuric acid, nitric acid, perchloric acid and phosphoric acid.

10. The process as claimed in claim 7, wherein the organic acid is selected from the group consisting of halosulfonic acid, halomethanesulfonic acid, halocarboxylic acid and trifluoromethanesulfonic acid.

11. The process as claimed in claim 10, wherein the organic acid is trifluoromethanesulfonic acid.

12. The process as claimed in claim 1, wherein nitrous oxide is used in a molar ratio relative to the halobenzene of from 1:1 to 10:1.

13. The process as claimed in claim 1, wherein the reaction is carried out at a temperature ranging from 300° to 500° C.

* * * * *